United States Patent
Josch et al.

(10) Patent No.: US 10,647,639 B2
(45) Date of Patent: May 12, 2020

(54) METHOD FOR PREPARING 1,3-BUTADIENE FROM N-BUTENES BY OXIDATIVE DEHYDROGENEATION

(71) Applicants: BASF SE, Ludwigshafen am Rhein (DE); Linde AG, München (DE)

(72) Inventors: Jan Pablo Josch, Ludwigshafen am Rhein (DE); Ragavendra Prasad Balegedde Ramachandran, Ludwigshafen am Rhein (DE); Ulrike Wenning, München (DE); Anton Wellenhofer, München (DE); Christine Toegel, München (DE); Hendrik Reyneke, München (DE); Heinz Boelt, München (DE)

(73) Assignees: BASF SE, Ludwigshafen am Rhein (DE); Linde AG, München (DE)

( * ) Notice: Subject to any disclaimer, the term of this patent is extended or adjusted under 35 U.S.C. 154(b) by 0 days.

(21) Appl. No.: 16/074,454

(22) PCT Filed: Jan. 30, 2017

(86) PCT No.: PCT/EP2017/051892
§ 371 (c)(1),
(2) Date: Aug. 1, 2018

(87) PCT Pub. No.: WO2017/133997
PCT Pub. Date: Aug. 10, 2017

(65) Prior Publication Data
US 2019/0039971 A1 Feb. 7, 2019

(30) Foreign Application Priority Data
Feb. 4, 2016 (EP) .................... 16154181

(51) Int. Cl.
*C07C 5/48* (2006.01)
*C07C 7/08* (2006.01)
(Continued)

(52) U.S. Cl.
CPC .................. *C07C 5/48* (2013.01); *C07C 7/08* (2013.01); *C07C 7/11* (2013.01); *C07C 11/08* (2013.01);
(Continued)

(58) Field of Classification Search
None
See application file for complete search history.

(56) References Cited

U.S. PATENT DOCUMENTS 3,911,039 A 10/1975 Grasselli et al.
3,932,551 A 1/1976 Grasselli et al.
(Continued)

FOREIGN PATENT DOCUMENTS

DE 2440329 A1 3/1975
DE 2447825 A1 8/1975
(Continued)

OTHER PUBLICATIONS

U.S. Appl. No. 15/780,725.
(Continued)

*Primary Examiner* — Ali Z Fadhel
(74) *Attorney, Agent, or Firm* — Drinker Biddle & Reath LLP (57) ABSTRACT

The invention relates to a method for producing butadiene from n-butenes having the steps:

A) providing an n-butene-comprising feed gas stream a;

B) feeding the n-butene-comprising feed gas stream a and an oxygen-comprising gas into at least one oxidative dehydrogenation zone and oxidatively dehydrogenating n-butenes to butadiene, wherein a product gas stream b comprising butadiene, unreacted n-butenes, steam, oxygen, low-boiling hydrocarbons, high-boiling minor components, optionally carbon oxides and optionally inert gases is obtained;

Ca) cooling the product gas stream b by contacting it with a refrigerant and condensing at least a part of the high-boiling minor components;

Cb) compressing the remaining product gas stream b in at least one compression step, wherein at least one aqueous condensate stream c1 and a gas stream c2 comprising butadiene, n-butenes, steam, oxygen, low-boiling hydrocarbons, optionally carbon oxides and optionally inert gases is obtained;

Da) separating off non-condensable and low-boiling gas components comprising oxygen, low-boiling hydrocarbons, optionally carbon oxides and optionally inert gases as gas stream d2 from the gas stream c2 by absorbing the $C_4$ hydrocarbons comprising butadiene and n-butenes in an absorption medium, wherein an absorption medium stream loaded with $C_4$ hydrocarbons and the gas stream d2 are obtained, and Db) subsequently desorbing the $C_4$ hydrocarbons from the loaded absorption medium stream in a desorption column, wherein a $C_4$ product gas stream d1 is obtained, Dc) separating off the steam condensate from the absorption medium in a phase separator and vaporizing it in a steam generator and providing it again as stripping gas in the desorption column, wherein, the steam condensate before the vaporization in a steam generator, is subjected to a pretreatment in a further method step.

9 Claims, 1 Drawing Sheet

(51) Int. Cl.
*C07C 7/11* (2006.01)
*C07C 11/08* (2006.01)
*C07C 11/167* (2006.01)

(52) U.S. Cl.
CPC ........ *C07C 11/167* (2013.01); *C07C 2523/31* (2013.01); *C07C 2523/86* (2013.01); *C07C 2523/881* (2013.01)

(56) References Cited

U.S. PATENT DOCUMENTS

| | | | |
|---|---|---|---|
| 3,956,181 | A | 5/1976 | Grasselli et al. |
| 4,162,234 | A | 7/1979 | Grasselli et al. |
| 4,336,409 | A | 6/1982 | Yamamoto et al. |
| 4,397,771 | A | 8/1983 | Grasselli et al. |
| 4,423,281 | A | 12/1983 | Yamamoto et al. |
| 4,424,141 | A | 1/1984 | Grasselli et al. |
| 4,547,615 | A | 10/1985 | Yamamoto |
| 9,957,208 | B2 | 5/2018 | Grune et al. |
| 2012/0130137 | A1 | 5/2012 | Orita et al. |
| 2017/0036972 | A1* | 2/2017 | Han ............ B01J 3/00 |
| 2017/0334809 | A1 | 11/2017 | Grune et al. |
| 2018/0002254 | A1 | 1/2018 | Josch et al. |
| 2018/0105479 | A1 | 4/2018 | Josch et al. |
| 2018/0282246 | A1 | 10/2018 | Ungelenk et al. |

FOREIGN PATENT DOCUMENTS

| | | |
|---|---|---|
| DE | 2530959 A1 | 2/1976 |
| DE | 2600128 A1 | 7/1976 |
| JP | 2010090083 A | 4/2010 |
| JP | 2011001341 A | 1/2011 |
| JP | 2011132218 A | 7/2011 |
| JP | 2012240963 A | 12/2012 |
| WO | WO-2014111406 A1 | 7/2014 |
| WO | WO-2014111409 A1 | 7/2014 |
| WO | WO-2016150738 A1 | 9/2016 |
| WO | WO-2016150940 A1 | 9/2016 |
| WO | WO-2016151033 A1 | 9/2016 |
| WO | WO-2016151074 A1 | 9/2016 |

OTHER PUBLICATIONS

U.S. Appl. No. 16/069,553.
International Search Report for PCT/EP2017/051892 dated Apr. 4, 2017.
Volkamer, K., et al., "Entwicklungsarbeiten am Butadien—verfahren der BASF", Erdöl und Kohle—Erdgas—Petrochemie, Band 34, Heft 8, (1981), pp. 343-346. (in German).
Weitz, H., et al., "Butadien", Ullmann's Enzyklopädie der Technischen Chemie, Band 9, Heft 4, (1975), pp. 1-18. (in German).
Written Opinion of the International Searching Authority for PCT/EP2017/051892 dated Apr. 4, 2017.

* cited by examiner

METHOD FOR PREPARING 1,3-BUTADIENE FROM N-BUTENES BY OXIDATIVE DEHYDROGENEATION

CROSS-REFERENCE TO RELATED APPLICATIONS

This application is a national stage application (under 35 U.S.C. § 371) of PCT/EP2017/051892, filed Jan. 30, 2017, which claims benefit of European Application No. 16154181.8, filed Feb. 4, 2016, both of which are incorporated herein by reference in their entirety.

The invention relates to a method for producing 1,3-butadiene from n-butenes by oxidative dehydrogenation (ODH).

Butadiene is an important key chemical and is used, for example, for producing synthetic rubbers (butadiene homopolymers, styrene-butadiene rubber or nitrile rubber) or for producing thermoplastic terpolymers (acrylonitrile-butadiene-styrene copolymers). Butadiene is further reacted to form sulfolane, chloroprene and 1,4-hexamethylenediamine (via 1,4-dichlorobutene and adipodinitrile). By dimerizing butadienes, in addition, vinylcyclohexene can be generated, which can be dehydrogenated to styrene.

Butadiene can be produced by thermal cracking (steam cracking) of saturated hydrocarbons, wherein, the procedure usually starts from naphtha as raw material. In the steam cracking of naphtha, a hydrocarbon mixture of methane, ethane, ethene, acetylene, propane, propene, propyne, allene, butanes, butenes, butadiene, butynes, methylallene, $C_5$ and higher hydrocarbons arises.

Butadiene can also be obtained by oxidative dehydrogenation of n-butenes (1-butene and/or 2-butene). Any desired n-butene-comprising mixture can be used as starting gas mixture for the oxidative dehydrogenation (oxydehydrogenation, ODH) of n-butenes to butadiene. For example, a fraction can be used which, as main component, comprises n-butenes (1-butene and/or 2-butene) and was obtained from the $C_4$ fraction of a naphtha cracker by separating off butadiene and isobutene. In addition, gas mixtures can also be used as starting gas, which mixtures comprise 1-butene, cis-2-butene, trans-2-butene or mixtures thereof and were obtained by dimerization of ethylene. In addition, as starting gas, n-butene-comprising gas mixtures can be used, which were obtained by catalytic fluid bed cracking (Fluid Catalytic Cracking, FCC).

Methods for oxidative dehydrogenation of butenes to form butadiene are known in principle. Such methods frequently comprise the following steps:

A) providing an n-butene-comprising feed gas stream a;
B) feeding the n-butene-comprising feed gas stream a and an oxygen-comprising gas into at least one oxidative dehydrogenation zone and oxidatively dehydrogenating n-butenes to butadiene, wherein a product gas stream b comprising butadiene, unreacted n-butenes, steam, oxygen, low-boiling hydrocarbons, high-boiling minor components, optionally carbon oxides and optionally inert gases is obtained;
Ca) cooling the product gas stream b by contacting it with a refrigerant and condensing at least a part of the high-boiling minor components;
Cb) compressing the remaining product gas stream b in at least one compression step, wherein at least one aqueous condensate stream c1 and a gas stream c2 comprising butadiene, n-butenes, steam, oxygen, low-boiling hydrocarbons, optionally carbon oxides and optionally inert gases is obtained;
Da) separating off non-condensable and low-boiling gas components comprising oxygen, low-boiling hydrocarbons, optionally carbon oxides and optionally inert gases as gas stream d2 from the gas stream c2 by absorbing the $C_4$ hydrocarbons comprising butadiene and n-butenes in an absorption medium, wherein an absorption medium stream loaded with $C_4$ hydrocarbons and the gas stream d2 are obtained, and
Db) subsequently desorbing the $C_4$ hydrocarbons from the loaded absorption medium stream in a desorption column, wherein a $C_4$ product gas stream d1 is obtained.

US 2012/0130137 A1, for example, describes a method for oxidative dehydrogenation of butenes to butadiene, using catalysts which comprise oxides of molybdenum, bismuth and generally further metals.

In paragraph [0122], reference is also made to the problems of byproducts. In particular, phthalic anhydride, anthraquinone and fluorenone are mentioned which are typically present in the product gas in concentrations from 0.001 to 0.10 vol.-%. In US 2012/0130137 A1 paragraph [0124] to [0126], it is advised to cool the hot reactor discharge gases directly by contact with a cooling liquid (quench tower) to first 5 to 100° C. As cooling liquids, water or aqueous alkali metal solutions are mentioned. Explicitly, the problems of blockages in the quench due to high boilers from the product gas or due to polymerization products of high-boiling byproducts from the product gas are mentioned, for which reason it is said to be advantageous that high-boiling byproducts are discharged as little as possible from the reaction part into the cooling part (quench). Separating off isobutene or the reaction product thereof methacrolein (hereinafter also abbreviated as MAC), acetaldehyde or acrolein, is not mentioned.

In JP 2011-001341 A a two-step cooling is described for a method for the oxidative dehydrogenation of alkenes to conjugated alkadienes. In this case, the product discharge gas of the oxidative dehydrogenation is first set to a temperature between 300 and 221° C. and is then further cooled to a temperature between 99 and 21° C. In paragraph [0066] ff. it is described that, to set the temperature between 300 and 221° C., heat exchangers are preferably used, wherein, however, some of the high-boilers from the product gas could also precipitate out in said heat exchangers. In JP 2011-001341 A, therefore, an occasional washing out of deposits from the heat exchangers using organic or aqueous solvents is described. As solvents, for example, aromatic hydrocarbons such as toluene or xylene or an alkaline aqueous solvent such as, for example, the aqueous solution of sodium hydroxide, are described. In order to avoid excessively frequent shutting down of the method for cleaning the heat exchanger, in JP 2011-001341 A, a structure having two parallel heat exchangers is described which are respectively alternately in operation or purged (what is termed A/B procedure). Separating off isobutene or the reaction product thereof methacrolein, from acetaldehyde or acrolein, is not mentioned.

JP 2011-132218 restricts the isobutene content in the feed, since it is known that isobutene forms oxygenates. Separating off the oxygenates, however, is not described.

JP 2012-240963 describes a method for butadiene production in which the $C_4$ hydrocarbon-containing gas stream is brought into contact with an absorbent b in an absorption step b', in order to absorb the $C_4$ components.

JP 2010-090083 restricts the amount of aldehydes and in table 1 also discloses the formation of methacrolein, but makes no proposals on separation off thereof.

Isobutene is present in virtually all $C_4$ hydrocarbon streams that can be used for the ODH process. In particular, $C_4$ hydrocarbon streams from FC crackers comprise isobutene in amounts of up to 15% by volume. The isobutene entering into the ODH reactor is, depending on the catalyst used and the reaction conditions, approximately 50% converted to methacrolein.

This accumulates in the circulating stream of the absorption/desorption part of the $C_4$ hydrocarbon separation and can cause side reactions such as oligomerizations and polymerizations, deposits on the column internals and in particular on evaporators and condensers, and also an impairment of the separation efficiency.

In addition, minor components lead to solids regularly depositing in the steam generator of the desorption column. These solids are formed in the steam generator from minor components present in the circulation water, inter alia, by coking or polymerization, and are deposited in the steam generator and also in downstream lines.

The object of the invention is to provide an improved method for producing butadiene by oxidative dehydrogenation of n-butenes and subsequent workup of the product gas stream comprising $C_4$ hydrocarbons and byproducts, which method remedies the above described disadvantages.

The object is achieved by a method for producing butadiene from n-butenes having the steps;

A) providing an n-butene-comprising feed gas stream a;
B) feeding the n-butene-comprising feed gas stream a and an oxygen-comprising gas into at least one oxidative dehydrogenation zone and oxidatively dehydrogenating n-butenes to butadiene, wherein a product gas stream b comprising butadiene, unreacted n-butenes, steam, oxygen, low-boiling hydrocarbons, high-boiling minor components, optionally carbon oxides and optionally inert gases is obtained;
Ca) cooling the product gas stream b by contacting it with a refrigerant and condensing at least a part of the high-boiling minor components;
Cb) compressing the remaining product gas stream b in at least one compression step, wherein at least one aqueous condensate stream c1 and a gas stream c2 comprising butadiene, n-butenes, steam, oxygen, low-boiling hydrocarbons, optionally carbon oxides and optionally inert gases is obtained;
Da) separating off non-condensable and low-boiling gas components comprising oxygen, low-boiling hydrocarbons, optionally carbon oxides and optionally inert gases as gas stream d2 from the gas stream c2 by absorbing the $C_4$ hydrocarbon-comprising butadiene and n-butenes in an absorption medium, wherein an absorption medium stream loaded with Ca hydrocarbons and the gas stream d2 are obtained, and
Db) subsequently desorbing the $C_4$ hydrocarbons from the loaded absorption medium stream in a desorption column by means of steam as stripping gas, wherein a $C_4$ product gas stream d1 is obtained and in the sump of the desorption column a liquid mixture of absorption medium and steam condensate is produced,
Dc) separating off the steam condensate from the absorption medium in a phase separator and vaporizing it in a steam generator and providing it again as stripping gas in the desorption column, wherein, the steam condensate before the vaporization in a steam generator, is subjected to a pretreatment in a further method step.

Surprisingly, it has been established that minor components having a low boiling point accumulate in the condensate of the stripping steam used in the desorption column, which minor components may be separated off, for example in a separate column. The minor components have a lower boiling point than water vapor. Minor components which can accumulate in the steam condensate of the desorption column are acrolein, methacrolein and 3-hydroxypropanal. The low-boiling minor components can be separated off from the steam condensate by stripping with a stripping gas, preferably nitrogen, by heating, preferably at a reduced pressure, or by a combination of both measures, before the condensate purified in this way is again fed to a steam generator for generating stripping steam. This pretreatment of the aqueous condensate stream counteracts a solids formation in the steam generator. Preferably, the minor components are separated off by stripping with nitrogen, preferably at a temperature in the range from 20 to 80° C., and at a pressure from 0.1 to 15 bar. The gas stream obtained at the top of the low-boiler separation column which comprises the minor components can be utilized thermally.

Generally, the concentration of the low-boiling minor components, that is to say the minor components with a boiling point lower than water, after the separation step according to the invention is carried out, is 0.1 to 1000 ppm, preferably 10 to 100 ppm. The content of the minor components acrylic acid, methacrylic acid and 3-propanal in total, is generally 0.1 to 500 ppm, preferably 1 to 100 ppm.

Preferably, the steps E) and F) are further carried out:

E) separating the $C_4$ product stream d1 by extractive distillation using a solvent selective for butadiene into a material stream e1 comprising butadiene and the selective solvent and a material stream e2 comprising n-butenes;
F) distilling the butadiene and the material stream e1 comprising the selective solvent into a material stream f1 substantially comprising the selective solvent and a material stream f2 comprising butadiene.

Generally, an aqueous refrigerant or an organic solvent is used in the cooling step Ca).

Preferably, an organic solvent is used in the cooling step Ca). The dissolving power for the high-boiling minor products that can leave sediments and blockages in the plant parts downstream of the ODH reactor is generally much higher in organic solvents than water or aqueous alkaline solutions. Preferred organic solvents used as refrigerants are aromatic hydrocarbons, for example toluene, o-xylene, m-xylene, p-xylene, diethylbenzenes, triethylbenzenes, diisopropylbenzenes, triisopropylbenzenes and mesitylene or mixtures thereof. Particular preference is given to mesitylene.

Embodiments hereinafter are preferred or particularly preferred variants of the method according to the invention.

The step Ca) is carried out in a multistep manner in steps Ca1) to Can), preferably in a two-step manner in two steps Ca1) and Ca2). In this case, particularly preferably, at least a part of the solvent, after it passes through the second step Ca2), is fed as coolant to the first step Ca1).

The step Cb) generally comprises at least one compression step Cba) and at least one cooling step Cbb). Preferably, at least one cooling step Cbb) in which the gas that was compressed in the compression step Cba) is brought into contact with a coolant. Particularly preferably, the coolant of the cooling step Cbb) comprises the same organic solvent that is used as coolant in the step Ca). In a particularly preferred variant, at least a part of said coolant, after it passes through the at least one cooling step Cbb) is fed as coolant to the step Ca).

Preferably, the step Cb) comprises a plurality of compression steps Cba1) to Cban) and cooling steps Cbb1) to Cbbn), for example four compression steps Cba1) to Cba4) and four cooling steps Cbb1) to Cbb4).

Preferably, step D) comprises steps Da1), Da2) and Db):

Da1) absorbing the butadiene comprising $C_4$ hydrocarbons and n-butenes in a high-boiling absorption medium, wherein an absorption medium stream loaded with $C_4$ hydrocarbons and the gas stream d2 are obtained, Da2) removing oxygen from the absorption medium stream from step Da) that is loaded with $C_4$ hydrocarbons by stripping with a non-condensable gas stream, and Db) desorbing the $C_4$ hydrocarbons from the loaded absorption medium stream, wherein a $C_4$ product gas stream d1 is obtained that substantially comprises $C_4$ hydrocarbons and comprises less than 100 ppm of oxygen.

Preferably, the high-boiling absorbent used in step Da) is an aromatic hydrocarbon solvent, particularly preferably it is the aromatic hydrocarbon solvent used in step Ca), in particular mesitylene. Diethylbenzenes, triethylbenzenes, diisopropylbenzenes and triisopropylbenzenes can also be used.

In an embodiment of the invention, at least 30%, preferably at least 40%, of the gas stream d2 present in step Da) is recirculated to step B). This can be expedient when only a small purge stream must be ejected from the gas stream d2.

Figure 1:
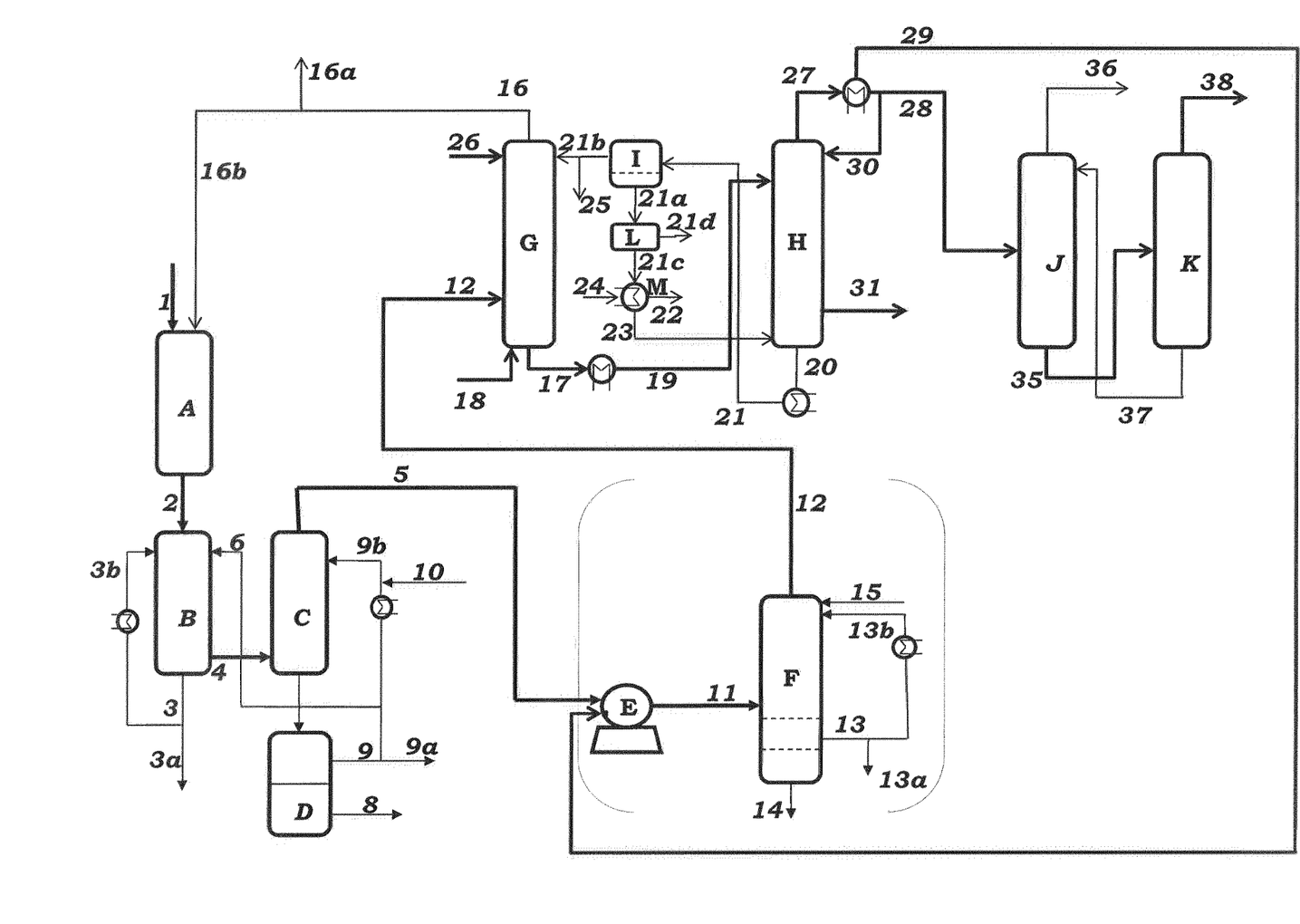

An embodiment of the method according to the invention is shown in FIG. 1 and is described in detail hereinafter.

As feed gas stream, n-butene-(1-butene and/or cis-/trans-2-butene) and isobutene-comprising gas mixtures are used. Such a gas mixture can be obtained, for example, by non-oxidative dehydrogenation of n-butane. A fraction can also be used which as main component comprises n-butenes (1-butene and cis-/trans-2-butene) and was obtained from the $C_4$ fraction of the naphtha cracking by separating off butadiene and isobutene. In addition, gas mixtures can also be used as starting gas stream that comprise 1-butene, cis-2-butene, trans-2-butene or mixtures thereof, and which were obtained by dimerizing ethylene. In addition, as starting gas stream, n-butene-comprising gas mixtures can be used that were obtained by fluid catalytic cracking (FCC).

In an embodiment of the method according to the invention, the n-butene-comprising starting gas mixture is obtained by non-oxidative dehydrogenation of n-butane. By the coupling of a non-oxidative catalytic dehydrogenation to the oxidative dehydrogenation of the n-butenes formed, a high yield of butadiene, based on n-butane used, can be obtained. In the non-oxidative catalytic n-butane dehydrogenation, a gas mixture is obtained that, in addition to butadiene, comprises 1-butene, 2-butene and unreacted n-butane minor components. Customary minor components are hydrogen, steam, nitrogen, CO and $CO_2$, methane, ethane, ethene, propane and propene. The composition of the gas mixture leaving the first dehydrogenation zone can vary greatly depending on the procedure of the dehydrogenation. For instance, when the dehydrogenation is carried out with feed-in of oxygen and additional hydrogen, the product gas mixture has a comparatively high content of steam and carbon oxides. In the case of procedures without feed-in of oxygen, the product gas mixture of the non-oxidative dehydrogenation has a comparatively high content of hydrogen.

In step B), the n-butene-comprising feed gas stream and an oxygen-comprising gas are fed into at least one dehydrogenation zone (the ODH reactor A) and the butenes present in the gas mixture are dehydrogenated oxidatively to butadiene in the presence of an oxydehydrogenation catalyst.

In an embodiment, it is preferred to use an oxygen-comprising gas that comprises more than 10% by volume, preferably more than 15% by volume, and particularly preferably more than 20% by volume, of molecular oxygen. In an embodiment, air is used as oxygen-comprising gas. The upper limit of the content of molecular oxygen in the oxygen-comprising gas is then generally 50% by volume or less, preferably 30% by volume or less, and still more preferably 25% by volume or less. Furthermore, any desired inert gases can be present in the molecular oxygen-comprising gas. Possible inert gases that may be mentioned are nitrogen, argon, neon, helium, CO, $CO_2$ and water. The amount of inert gases in the oxygen-comprising gas is, for nitrogen, generally 90% by volume or less, preferably 85% by volume or less, and still more preferably 80% by volume or less. In the case of components other than nitrogen in the oxygen-comprising gas, they are generally 10% by volume or less, preferably 1% by volume or less.

Catalysts suitable for the oxydehydrogenation are generally based on a Mo—Bi—O-comprising multimetal oxide system that generally additionally comprises iron. Generally, the catalyst system comprises still further additional components such as, for example, potassium, cesium, magnesium, zirconium, chromium, nickel, cobalt, cadmium, tin, lead, germanium, lanthanum, manganese, tungsten, phosphorus, cerium, aluminum or silicon. Iron-comprising ferrites have also been proposed as catalysts.

In a preferred embodiment, the multimetal oxide comprises cobalt and/or nickel. In a further preferred embodiment, the multimetal oxide comprises chromium. In a further preferred embodiment, the multimetal oxide comprises manganese.

Examples of Mo—Bi—Fe—O-comprising multimetal oxides are Mo—Bi—Fe—Cr—O— or Mo—Bi—Fe—Zr—O— comprising multimetal oxides. Preferred systems are, for example, described in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3Co_{4.5}Ni_{2.5}P_{0.5}K_{0.1}O_x$+$SiO_2$), DE-A 25 30 959 ($Mo_{12}BiFe_3Co_{4.5}Ni_{2.5}Cr_{0.5}K_{0.1}O_x$, $Mo_{13.75}BeFe_3Co_{4.5}Ni_{2.5}Ge_{0.5}K_{0.8}O_x$, $Mo_{12}BiFe_3Co_{4.5}Ni_{2.5}Mn_{0.5}K_{0.1}O_x$ and $Mo_{12}BiFe_3Co_{4.5}Ni_{2.5}La_{0.5}K_{0.1}O_x$), U.S. Pat. No. 3,911,039 ($Mo_{12}BiFe_3Co_{4.5}Ni_{2.5}Sn_{0.5}K_{0.1}O_x$), DE-A 25 30 959 and DE-A 24 47 825 ($Mo_{12}BiFe_3Co_{4.5}Ni_{2.5}W_{0.5}K_{0.1}O_x$).

Suitable multimetal oxides and production thereof are in addition described in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x$+$SiO_2$) and DE-A 24 40 329 ($Mo_{12}BiCo_{4.5}Ni_{2.5}Cr_3P_{0.5}K_{0.1}O_x$).

Particularly preferred catalytically active multimetal oxides comprising molybdenum and at least one further metal have the general formula (Ia):

$$Mo_{12}Bi_aFe_bCo_cNi_dCr_eX^1_fX^2_gO_y \qquad (Ia)$$

where
$X^1$=Si, Mn and/or Al,
$X^2$=Li, Na, K, Cs and/or Rb,
$0.2 \leq a \leq 1$,
$0.5 \leq b \leq 10$,
$0 \leq c \leq 10$,
$0 \leq d \leq 10$, $2 \leq c+d \leq 10$,
$0 \leq e \leq 2$,
$0 \leq f \leq 10$,
$0 \leq g \leq 0.5$, y=a number which is determined, assuming charge neutrality, by the valency and frequency in (Ia) of the elements different from oxygen.

Preference is given to catalysts, the catalytically active oxide mass of which has, of the two metals Co and Ni, only Co (d=0). Preferably, $X^1$ is Si and/or Mn and $X^2$ is preferably K, Na and/or Cs, particularly preferably $X^2$=K. Particular preference is given to a substantially Cr(VI)-free catalyst.

To carry out the oxidative dehydrogenation with a high overall conversion rate of n-butenes, a gas mixture is preferred which has a molar oxygen: n-butenes ratio of at least 0.5. Preferably, an oxygen: n-butenes ratio from 0.55 to 10 is employed. To set this value, the starting gas can be mixed with oxygen or an oxygen-comprising gas and optionally additional inert gas, methane or steam. The resultant oxygen-comprising gas mixture is then fed to the oxydehydrogenation.

The reaction temperature of the oxydehydrogenation is generally controlled by a heat-exchange medium which is situated around the reaction tubes. As such liquid heat-exchange media, e.g. melts of salts or salt mixtures such as potassium nitrate, potassium nitrite, sodium nitrite and/or sodium nitrate, and also melts of metals such as sodium, mercury and alloys of various metals come into consideration. However, ionic liquids or heat-transfer oils are also usable. The temperature of the heat-exchange medium is between 220 and 490° C., and preferably between 300 and 450° C., and particularly preferably between 350 and 420° C.

On account of the exothermy of the reactions proceeding, the temperature can be higher during the reaction in certain sections of the reaction interior than that of the heat-exchange medium, and what is termed a hot spot is formed. The position and level of the hot spot is established by the reaction conditions, but it can also be regulated by the dilution ratio of the catalyst layer or the flow rate of mixed gas. The difference between hot spot temperature and the temperature of the heat-exchange medium is generally between 1 and 150° C., preferably between 10 and 100° C., and particularly preferably between 20 and 80° C. The temperature at the end of the catalyst bed is generally between 0 to 100° C., preferably between 0.1 and 50° C., particularly preferably between 1 and 25° C. above the temperature of the heat-exchange medium.

The oxydehydrogenation can be carried out in all fixed-bed reactors known from the prior art such as, for example, in multiple-half furnaces, in fixed-bed tubular reactors or tube-bundle reactors, or in the plate heat-exchange reactor. A tube-bundle reactor is preferred.

Preferably, the oxidative dehydrogenation is carried out in fixed-bed tubular reactors or fixed-bed tube-bundle reactors. The reaction tubes are generally (just as are the other elements of the tube-bundle reactor) made of steel. The wall thickness of the reaction tubes is typically 1 to 3 mm. The internal diameter thereof is generally (uniformly) 10 to 50 mm, or 15 to 40 mm, frequently 20 to 30 mm. The number of reaction tubes accommodated in the tube-bundle reactor is generally at least 1000, or 3000 or 5000, preferably at least 10 000. Frequently, the number of reaction tubes accommodated in the tube-bundle reactor is 15 000 to 30 000, or up to 40 000, or up to 50 000. The length of the reaction tube is usually a few meters, typically a reaction tube length is in the range from 1 to 8 m, commonly 2 to 7 m, frequently 2.5 to 6 m.

In addition, the catalyst layer which is installed in the ODH-reactor A can comprise a single layer or two or more layers. These layers can comprise a pure catalyst, or be diluted with a material that does not react with the starting gas or components of the product gas of the reaction. In addition, the catalyst layers can comprise solid material and/or supported shell catalysts.

The product gas stream 2 leaving the oxidative dehydrogenation comprises, in addition to butadiene, generally unreacted 1-butene and 2-butene, oxygen, and also steam. As minor components, it additionally comprises, generally, carbon monoxide, carbon dioxide, inert gases (principally nitrogen), low-boiling hydrocarbons such as methane, ethane, ethene, propane and propene, butane and isobutane, optionally hydrogen and also optionally oxygen-comprising hydrocarbons, termed oxygenates. Oxygenates can be, for example, formaldehyde, furan, acetic acid, maleic anhydride, formic acid, methacrolein, methacrylic acid, crotonaldehyde, crotonic acid, propionic acid, acrylic acid, methyl vinyl ketone, styrene, benzaldehyde, benzoic acid, phthalic anhydride, fluorenone, anthraquinone and butyraldehyde.

The product gas stream 2 at the reactor discharge is characterized by a temperature close to the temperature at the end of the catalyst bed. The product gas stream is then brought to a temperature from 150 to 400° C., preferably 160 to 300° C., particularly preferably 170 to 250° C. It is possible to insulate the line through which the product gas stream flows or use a heat exchanger in order to maintain the temperature in the desired range. This heat-exchange system is of any desired type, provided that, using this system, the temperature of the product gas can be kept at the desired level. As an example of a heat exchanger, spiral heat exchangers, plate heat exchangers, double-tube heat exchangers, multiple-tube heat exchangers, kettle-spiral heat exchangers, kettle-shell heat exchangers, liquid-liquid contact heat exchangers, air heat exchangers, direct contact heat exchangers and also finned tubular heat exchangers may be mentioned. Since, while the temperature of the product gas is being set to the desired temperature, a part of the high-boiling byproducts which are present in the product gas can precipitate out, the heat-exchange system should therefore preferably have two or more heat exchangers. If in this case two or more heat exchangers provided are arranged in parallel, and a distributed cooling of the product gas obtained is thus permitted in the heat exchangers, the amount of high-boiling by products that are deposited in the heat exchangers falls, and the operating life thereof can be prolonged. As an alternative to the abovementioned method, the two or more heat exchangers provided can be arranged in parallel. The product gas is fed to one or more, but not all, heat exchangers, which, after a certain operating time, can be relieved by other heat exchangers. In this method, the cooling can be continued, a part of the heat of reaction recovered, and, in parallel thereto, the high-boiling byproducts that are deposited in one of the heat exchangers can be removed. As an abovementioned refrigerant, a solvent can be used, provided that it is able to dissolve the high-boiling byproducts. Examples are aromatic hydrocarbon solvents such as, e.g., toluene, xylenes, diethylbenzenes, triethylbenzenes, diisopropylbenzenes and triisopropylbenzenes. Particular preference is given to mesitylene. Aqueous solvents can also be used. These can be made either acidic or else alkaline, such as, for example, an aqueous solution of sodium hydroxide.

Then, a majority of the high-boiling minor components and the water are separated off from the product gas stream 2 by cooling and compression. The cooling proceeds via contacting with a refrigerant. This step is hereinafter also termed quench. This quench can comprise only one step or a plurality of steps (for example B, C in FIG. 1). The product gas stream 2 is therefore directly contacted with the organic cooling medium 3b and 9b and thereby cooled. Suitable cooling media are aqueous refrigerants or organic solvents, preferably aromatic hydrocarbons, particularly preferably toluene, o-xylene, m-xylene, p-xylene or mesitylene, or mixtures thereof. Diethylbenzene, triethylbenzene, diisopropylbenzene and triisopropylbenzene can also be used.

Preference is given to a two-step quench (comprising steps B and C as per FIG. 1), i.e. step Ca) comprises two cooling steps Ca1) and Ca2) in which the product gas stream 2 is contacted with the organic solvent.

Generally, the product gas 2, depending on presence and temperature level of a heat exchanger upstream of the quench B, has a temperature from 100 to 440° C. The product gas is contacted in the $1^{st}$ quenching step B with the cooling medium of organic solvent.

In this case, the cooling medium can be introduced via a nozzle in order to achieve an efficient as possible thorough mixing with the product gas. For the same purpose, internals, such as, for example, further nozzles, can be introduced in the quench step, through which internals the product gas and the cooling medium pass together. The refrigerant inlet into the quench is designed in such a manner that a blockage due to deposits in the region of the refrigerant inlet is minimized.

Generally, the product gas 2 is cooled in the first quench step B to 5 to 180° C., preferably to 30 to 130° C., and still more preferably to 60 to 110° C. The temperature of the refrigerant medium 3b at the inlet can generally be 25 to 200° C., preferably 40 to 120° C., particularly preferably 50 to 90° C. The pressure in the first quench step B is not particularly restricted, but is generally 0.01 to 4 bar (gage), preferably 0.1 to 2 bar (gage) and particularly preferably 0.2 to 1 bar (gage). If relatively large amounts of high-boiling byproducts are present in the product gas, polymerization of high-boiling byproducts and deposits of solids which are caused by high-boiling byproducts in this process step can readily occur. Generally, the quench step B is designed as a cooling tower. The cooling medium 3b used in the cooling tower is frequently used in circulation. The circuit stream of the cooling medium in liters per hour, based on the mass flow rate of butadiene in grams per hour, can generally be 0.0001 to 5 l/g, preferably 0.001 to 1 l/g, and particularly preferably 0.002 to 0.2 l/g.

The temperature of the cooling medium 3 in the sump can be generally 27 to 210° C., preferably 45 to 130° C., particularly preferably 55 to 95° C. Since the loading of the cooling medium 4 with minor components increases in the course of time, a part of the loaded cooling medium can be taken off from the circulation as purge stream 3a and the amount circulated can be kept constant by addition of unloaded cooling medium 6. The ratio of the amount removed and amount added depends on the steam loading of the product gas and the product gas temperature at the end of the first quench step.

The cooled product gas stream 4 that is possibly depleted in minor components can then be fed to a second quench step C. Therein, it can then again be brought into contact with a cooling medium 9b.

Generally, the product gas is cooled up to the gas exit of the second quench step C to 5 to 100° C., preferably to 15 to 85° C., and still more preferably to 30 to 70° C. The refrigerant can be fed in counterflow to the product gas. In this case, the temperature of the refrigerant medium 9b at the refrigerant inlet can be 5 to 100° C., preferably 15 to 85° C., particularly preferably 30 to 70° C. The pressure in the second quench step C is not particularly restricted, but is generally 0.01 to 4 bar (gage), preferably 0.1 to 2 bar (gage) and particularly preferably 0.2 to 1 bar (gage). The second quench step is preferably designed as a cooling tower. The cooling medium 9b used in the cooling tower is frequently used in circulation. The circuit stream of the cooling medium 9b in liters per hour, based on the mass flow rate of butadiene in grams per hour, can be generally 0.0001 to 5 l/g, preferably 0.001 to 1 l/g, and particularly preferably 0.002 to 0.2 l/g.

Depending on temperature, pressure, refrigerant and water content of the product gas 4, condensation of water can occur in the second quench step C. In this case, an additional aqueous phase 8 may form which can additionally comprise water-soluble minor components. These can then be taken off in the phase separator D. The temperature of the cooling medium 9 in the sump can generally be 20 to 210° C., preferably 35 to 120° C., particularly preferably 45 to 85° C. Since the loading of the cooling medium 9 with minor components increases in the course of time, a part of the loaded cooling medium can be taken off from the circulation as purge stream 9a, and the amount circulated can be kept constant by addition of unloaded cooling medium 10.

In order to achieve contact as good as possible between product gas and cooling medium, internals can be present in the second quench step C. Such internals comprise, for example, bubble-cap, centrifugal, and/or sieve trays, columns having structured packings, e.g. sheet-metal packings having a specific surface area from 100 to 1000 $m^2/m^3$ such as Mellapak® 250 Y, and randomly packed columns.

The solvent circuits of the two quench steps can be either separate from one another or connected to one another. Thus, for example stream 9a can be fed to stream 3b, or replace it. The desired temperature of the circuit streams can be set via suitable heat exchangers.

In a preferred embodiment of the invention, therefore, the cooling step Ca) is carried out in a two-step manner, wherein the solvent of the second step Ca2) that is loaded with minor components is conducted into the first step Ca1). The solvent withdrawn from the second step Ca2) comprises less minor components than the solvent withdrawn from the first step Ca1).

In order to minimize the entrainment of liquid components from the quench into the off-gas line, suitable structural measures can be made, such as, for example, the installation of a demister. In addition, high-boiling substances which are not separated off from the product gas in the quench can be removed from the product gas by further structural measures, such as, for example, further gas scrubbing operations.

A gas stream 5 is obtained which comprises n-butane, 1-butene, 2-butene, butadiene, optionally oxygen, hydrogen, water vapor, in small amounts methane, ethane, ethene, propane and propene, isobutane, carbon oxides, inert gases and parts of the solvent used in the quench. In addition, in this gas stream 5, traces of high-boiling components remain which cannot be separated off quantitatively in the quench.

Then, the gas stream b from the cooling step Ca) that is depleted in high-boiling minor components, is cooled in step Cb) in at least one compression step Cba) and preferably in at least one cooling step Cbb) by contacting it with an organic solvent as coolant.

The product gas stream 5 from the solvent quench is compressed in at least one compression step E and then further cooled in the cooling apparatus F, wherein at least one condensate stream 14 is formed. A gas stream 12 remains comprising butadiene, 1-butene, 2-butenes, oxygen, steam, optionally low-boiling hydrocarbons such as methane, ethane, ethene, propane and propene, butane and isobutane, optionally carbon oxides and optionally inert gases. In addition, said product gas stream can still comprise traces of high-boiling components.

The compression and cooling of the gas stream 5 can proceed in a single-step or multistep (n-step) manner. Generally, overall, compression proceeds from a pressure in the range from 1.0 to 4.0 bar (absolute) to a pressure in the range from 3.5 to 20 bar (absolute). After each compression step, there follows a cooling step, in which the gas stream is cooled to a temperature in the range from 15 to 60° C. The condensate stream can therefore, in the case of multistep compression, also comprise a plurality of streams. The condensate stream comprises in the main water and the solvent used in the quench. Both streams (aqueous and organic phases) can in addition comprise, to a small extent, minor components such as low-boilers, $C_4$ hydrocarbons, oxygenates and carbon oxides.

To cool the stream 11 formed by compressing stream 5, and/or to remove further minor components from the stream 11, the condensed quench solvent can be cooled in a heat exchanger and recirculated as refrigerant to apparatus F. Since the loading of this cooling medium 13b with minor components increases in the course of time, a part of the loaded cooling medium can be taken off from the circulation (13a) and the amount in circulation of the cooling medium can be kept constant by addition of unloaded solvent (15).

The solvent 15 which is added as cooling medium can be an aqueous refrigerant or an organic solvent. Preference is given to aromatic hydrocarbons, particular preference to toluene, o-xylene, m-xylene, p-xylene, diethylbenzene, triethylbenzene, diisopropylbenzene, triisopropylbenzene, mesitylene or mixtures thereof. Particular preference is given to mesitylene.

The condensate stream 13a can be recirculated to the circuit stream 3b and/or 9b of the quench. As a result, the $C_4$ components absorbed in the condensate stream 13a can again be brought into the gas stream and thereby the yield increased.

Suitable compressors are, for example, turbo compressors, rotary piston compressors and reciprocating piston compressors. The compressors can be driven, for example, with an electric motor, an expander or a gas or steam turbine. The intake pressure into the first compressor step is 0.5 to 3 bar absolute, preferably 1 to 2 bar absolute. Typical compression ratios (exit pressure:entry pressure) per compressor step, depending on the type, are between 1.5 and 3.0.

The cooling of the compressed gas proceeds in refrigerant-purged heat exchangers or organic quench steps which can be designed, for example, as tube-bundle, spiral or plate heat exchangers. Suitable refrigerants can be aqueous solvents or the abovementioned organic solvents. As refrigerants in the heat exchangers, in this case cooling water or heat-carrier oils or organic solvents are used. In addition, preferably air cooling with the use of blowers is employed.

The gas stream 12 comprising butadiene, n-butenes, oxygen, low-boiling hydrocarbons (methane, ethane, ethene, propane, propene, n-butane, isobutane), optionally steam, optionally carbon oxides, and also optionally inert gases and optionally traces of minor components is fed as output stream for further processing.

In a step D), non-condensable and low-boiling gas components comprising oxygen, low-boiling hydrocarbons (methane, ethane, ethene, propane, propene), carbon oxides and inert gases are separated off from the process gas stream 12 as gas stream 16 in an absorption column G by absorbing the $C_4$ hydrocarbons in a high-boiling absorption medium (21b and/or 26) and subsequent desorption of the $C_4$ hydrocarbons. Preferably, the step D), as shown in FIG. 1, comprises the steps Da1), Da2) and Db):

Da1) absorbing the butadiene comprising $C_4$ hydrocarbons and n-butenes in a high-boiling absorption medium (21b and/or 26), wherein an absorption medium stream loaded with $C_4$ hydrocarbons and the gas stream 16 are obtained, Da2) removing oxygen from the absorption medium stream from step Da1) that is loaded with $C_4$ hydrocarbons by stripping with a non-condensable gas stream 18, wherein an absorption medium stream 17 loaded with $C_4$ hydrocarbons is obtained, and Db) desorbing the $C_4$ hydrocarbons from the loaded absorption medium stream, wherein a $C_4$ product gas stream 27 is obtained which comprises substantially $C_4$ hydrocarbons.

For this purpose, in the absorption step G the gas stream 12 is contacted with an absorption medium and the $C_4$ hydrocarbons are absorbed in the absorption medium, wherein an absorption medium loaded with $C_4$ hydrocarbons and an off-gas 16 comprising the remaining gas components are obtained. In a desorption step H, the $C_4$ hydrocarbons from the high-boiling absorption medium are liberated.

The absorption step can be carried out in any suitable absorption column known to those skilled in the art. The absorption can proceed by simply passing the product gas stream through the absorption medium. However, it can also proceed in columns or in rotary absorbers. The procedure can be carried out in cocurrent flow, countercurrent flow or cross flow. Preferably, the absorption is carried out in countercurrent flow. Suitable absorption columns are, e.g., tray columns having bubble-cap, centrifugal and/or sieve trays, columns having structured packings, e.g. sheet-metal packings having a specific surface area from 100 to 1000 $m^2/m^3$ such as Mellapak® 250 Y, and randomly packed columns. However, trickling towers and spray towers, graphite block absorbers, surface absorbers such as thick-layer and thin-layer absorbers and also rotary columns, disc scrubbers, cross-spray scrubbers and rotary scrubbers also come into consideration.

In an embodiment, the gas stream 12 comprising butadiene, n-butenes and the low-boiling and non-condensable gas components is fed to an absorption column in the lower region. In the upper region of the absorption column, the high-boiling absorption medium (21b and/or 26) is applied.

Inert absorption media used in the absorption step are generally high-boiling nonpolar solvents in which the $C_4$ hydrocarbon mixture that is to be separated off has a markedly higher solubility than the remaining gas components that are to be separated off. Suitable absorption media are comparatively nonpolar organic solvents, for example aliphatic $C_8$ to $C_{18}$ alkanes, or aromatic hydrocarbons such as the middle oil fractions from paraffin distillation, toluene or ethers with bulky groups, or mixtures of these solvents, wherein a polar solvent such as 1,2-dimethyl phthalate can be added thereto. Suitable absorption media are, in addition, esters of benzoic acid and phthalic acid with straight-chain $C_1$ to $C_8$ alkanols, and also what are termed heat-carrier oils, such as biphenyl and diphenyl ether, the chlorine derivatives thereof and also triarylalkenes. A suitable absorption medium is a mixture of biphenyl and diphenyl ether, preferably in the azeotropic composition, for example the commercially available Diphyl®. Frequently this solvent mixture comprises dimethyl phthalate in an amount from 0.1 to 25% by weight.

In a preferred embodiment in the absorption step Da1), the same solvent is used as in the cooling step Ca).

Preferred absorption media are solvents that have a dissolving power for organic peroxides of at least 1000 ppm (mg of active oxygen/kg of solvent). Preference is given to aromatic hydrocarbons, particular preference to toluene, o-xylene, p-xylene and mesitylene, or mixtures thereof. Diethylbenzene, triethylbenzene, diisopropylbenzene and triisopropylbenzene can also be used.

At the top of the absorption column G, a stream 16 is taken off that comprises substantially oxygen, low-boiling hydrocarbons (methane, ethane, ethene, propane, propene), optionally $C_4$ hydrocarbons (butane, butenes, butadiene), optionally inert gases, optionally carbon oxides, and optionally also steam. This material stream can be fed in part to the ODH reactor. Thereby, for example the intake stream of the ODH reactor may be set to the desired $C_4$ hydrocarbon content.

At the sump of the absorption column, by the purging with a gas 18, residues of oxygen dissolved in the absorption medium are discharged. The remaining oxygen fraction shall be so small that the stream 27 that is leaving the desorption column and comprises butane, butene and butadiene only still comprises a maximum of 100 ppm of oxygen.

Stripping out the oxygen in step Db) can be carried out in any suitable column known to those skilled in the art. The stripping can be performed by simply passing non-condensable gases, preferably gases such as methane that are non-absorbable or only weakly absorbable in the absorption medium stream 21b and/or 26, through the loaded absorption solution. $C_4$ hydrocarbons that are conjointly stripped out are backwashed into the absorption solution in the upper part of the column G by passing the gas stream back into this absorption column. This can be performed either via pipework of the stripping column or by direct mounting of the stripping column beneath the absorber column. Since the pressure in the stripping column part and the absorption column part is identical, this direct coupling can proceed. Suitable stripping columns are, e.g., tray columns having bubble-cap, centrifugal and/or sieve trays, columns having structured packings, e.g. sheet-metal packings having a specific surface area from 100 to 1000 $m^2/m^3$ such as Mellapak® 250 Y, and randomly packed columns. However, trickling towers and spray towers and also rotary columns, disc scrubbers, cross-spray scrubbers and rotary scrubbers also come into consideration. Suitable gases are, for example, nitrogen or methane.

The stream 17 can optionally be cooled or heated and enters as stream 19 into the desorption column. The entry point is generally 0 to 10 theoretical plates, preferably 2 to 8, particularly preferably 3 to 5 theoretical plates below the column top.

The absorption medium that is regenerated in the desorption step is withdrawn at the column sump in the mixture with the condensed stripping steam as stream 20 of the desorption column H. This two-phase mixture can be cooled in a heat exchanger and is fed as stream 21 to a phase separator I constructed as a decanter. There, the stream 21 is separated into an aqueous stream 21a and an organic absorption medium stream 21b. The regenerated absorption medium stream 21b is fed again to the absorption column G. Low boilers such as, for example, ethane or propane, and also high-boiling components such as benzaldehyde, maleic anhydride and phthalic anhydride that are present in the process gas stream can accumulate in the absorption medium circuit stream. In order to restrict the accumulation, a purge stream 25 can be taken off.

In an embodiment of the invention, the condensate stream 21a that occurs from the dehydrogenation plant is fed in whole or in part to an effluent treatment plant. In the effluent treatment plant which can comprise a chemical and/or biological purification step, the condensate stream is purified and disposed of in accordance with the local conditions in the context of the overall waste water stream. A substance flow of suitable raw water equivalent to the condensate stream removed is fed into the dehydrogenation plant, after any required treatment (such as, for example, complete demineralization) and then vaporized in the steam generator.

This embodiment with complete processing of the condensate outside the dehydrogenation plant has the advantage that, by utilizing the pre-existing infrastructure of a petrochemical complex, no additional capital costs arise in the context of the dehydrogenation plant.

In a preferred embodiment, the aqueous stream 21a for water treatment, before vaporization thereof, is fed according to the invention only into a low-boiler separation column L. Suitable columns are, e.g., tray columns having bubble-cap, centrifugal and/or sieve trays, columns having structured packings, e.g. sheet-metal packings having a specific surface area from 100 to 1000 $m^2/m^3$ such as Mellapak® 250 Y, and randomly packed columns. There, by heating and stripping with nitrogen, low-boilers, in particular acrolein, present in the aqueous stream 21a are separated off as stream 21d. The resultant water stream 21c that is depleted in low-boilers is vaporized in the steam generator M, the stripping steam thus generated is fed into the desorption column as stream 23. In addition, a freshwater stream 24 can further be fed into the steam generator 23. Also, it is possible to vaporize only a part of stream 21c and take off the other part as stream 22 and, for example, feed it to the waste water treatment.

The $C_4$ product gas stream 27 substantially comprising n-butane, n-butenes and butadiene generally comprises 20 to 80% by volume butadiene, 0 to 80% by volume n-butane, 0 to 10% by volume 1-butene and 0 to 50% by volume 2-butenes, wherein the total amount gives 100% by volume. In addition, small amounts of isobutane can be present.

A part of the condensed overhead discharge of the desorption column H principally comprising $C_4$ hydrocarbons is recirculated to the column top as stream 30, in order to increase the separation efficiency of the column.

The desorption step H can be carried out in any desired suitable desorption column known to those skilled in the art. The desorption can be performed by reducing the pressure and/or heating the desorption step.

Suitable desorption columns are, e.g., tray columns having bubble-cap, centrifugal and/or sieve trays, columns having structured packings, e.g. sheet-metal packings having a specific surface area from 100 to 1000 $m^2/m^3$ such as Mellapak® 250 Y, and randomly packed columns. As shown in FIG. 1, a side takeoff stream 31 comprising methacrolein can be withdrawn from the desorption column H, in order to prevent the accumulation of methacrolein in the absorption medium circuit stream. The side takeoff stream 31 can be either liquid or else gaseous, preferably it is gaseous.

Preferably, the desorption column has 5 to 30, particularly preferably 10 to 20, theoretical plates. The side takeoff stream 31 is in this case preferably withdrawn in the lower third of the desorption column. The liquid side takeoff stream 31 generally comprises 0.1 to 2% by weight methacrolein. In addition, it comprises 5 to 15% by weight water, 0 to 3% by weight $C_4$ hydrocarbons and 70 to 90% by weight of the absorption medium.

The gaseous side takeoff stream 31 generally comprises 1 to 10% by weight of methacrolein. In addition, it comprises 30 to 60% by weight of water, 0 to 6% by weight of $C_4$ hydrocarbons and 30 to 60% by weight of the absorption medium.

The gaseous stream 29 comprising $C_4$ hydrocarbons is recirculated to the compressor, The liquid $C_4$ product stream 28 leaving the condenser is then separated in step E) by extractive distillation using a solvent selective for butadiene into a material stream 35 comprising butadiene and the selective solvent and a material stream 36 comprising butanes and n-butenes.

In an embodiment, the stream 28 can be washed in advance in a liquid-liquid washing with polyalcohols such as ethylene glycol and glycerol, or else methanol, and thus furan can in part be separated off. In a further embodiment, the stream 28 can be freed in advance from other minor components such as aldehydes in a gas-liquid scrubbing with water.

The extractive distillation can be carried out, for example, as described in "Erdöl and Kohle Erdgas—Petrochemie" [Petroleum and Coal—Natural Gas—Petrochemistry], volume 34 (8), pages 343 to 346 or "Ullmanns Enzyklopädie der Technischen Chemie" [Ullmann's Encyclopedia of Industrial Chemistry], volume 9, $4^{th}$ edition 1975, pages 1 to 18. For this purpose, the $C_4$ product gas stream is contacted with an extraction medium, preferably a N-methylpyrrolidone (NMP)/water mixture, in an extraction zone. The extraction zone is generally implemented in the form of a scrubbing column which comprises trays, random packings or structured packings as internals. This generally has 30 to 70 theoretical plates, in order that sufficiently good separation efficiency is achieved. Preferably, the scrubbing column of the column top has a backwash zone. This backwash zone serves for recovery of the extraction medium present in the gas phase using a liquid hydrocarbon reflux, wherein the overhead fraction is condensed in advance. The mass ratio of extraction medium to $C_4$ product gas stream in the feed of the extraction zone is generally 10:1 to 20:1. The extractive distillation is preferably operated at a sump temperature in the range from 100 to 250° C., in particular at a temperature in the range from 110 to 210° C., a top temperature in the range from 10 to 100° C., in particular in the range from 20 to 70° C. and a pressure in the range from 1 to 15 bar, in particular in the range from 3 to 8 bar. The extractive distillation column preferably has 5 to 70 theoretical plates.

Suitable extraction media are butyrolactone, nitriles such as acetonitrile, propionitrile, methoxypropionitrile, ketones such as acetone, furfural, N-alkyl substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, in particular N-methylpyrrolidone (NMP). Generally, alkyl-substituted lower aliphatic acid amides or N-alkyl substituted cyclic acid amides are used. Particularly advantageous are dimethylformamide, acetonitrile, furfural, and, in particular, NMP.

However, mixtures of these extraction media with one another, e.g. of NMP and acetonitrile, mixtures of these extraction media with co-solvents and/or tert-butyl ethers, e.g. methyl tert-butyl ether, ethyl tert-butyl ether, propyl tert-butyl ether, n-butyl or isobutyl tert-butyl ether can also be used. Particularly suitable is NMP, preferably in aqueous solution, preferably with 0 to 20% by weight of water, particularly preferably with 7 to 10% by weight of water, in particular with 8.3% by weight of water.

The overhead product stream 36 of the extractive distillation column J comprises substantially butane and butenes and in small amounts butadiene, and is taken off in the gaseous or liquid state. Generally, the stream substantially consisting of n-butane and 2-butene comprises up to 100% by volume of n-butane, 0 to 50% by volume of 2-butene and 0 to 3% by volume of further components such as isobutane, isobutene, propane, propene and $C_5^+$ hydrocarbons.

The stream 36 substantially comprising n-butane and 2-butene and optionally methane can be fed in whole or in part or else not to the $C_4$ feed of the ODH reactor. Since the butene isomers of this reflux stream substantially comprise 2-butenes and 2-butenes generally are oxidatively dehydrogenated more slowly to butadiene than 1-butene, this reflux stream can be isomerized catalytically before it is fed to the ODH reactor. As a result, the isomeric distribution can be set according to the isomeric distribution present at thermodynamic equilibrium. In addition, the stream can also be fed to a further workup, in order to separate butanes and butenes from one another and to recirculate the butenes in whole or in part to the oxydehydrogenation. The stream can also pass into the maleic anhydride production.

In a step F), the material stream 35 comprising butadiene and the selective solvent is separated by distillation into a material stream 37 substantially comprising the selective solvent and a butadiene-comprising material stream 38.

The material stream 35 obtained at the sump of the extractive distillation column J generally comprises the extraction medium, water, butadiene and, in small fractions, butenes and butane, and is fed to a distillation column K. Therein, butadiene can be obtained overhead or as a side takeoff. At the sump of the distillation column, a material stream 37 arises that comprises an extraction medium and optionally water, wherein the composition of the material stream comprising extraction medium and water corresponds to the composition as is added in the extraction. The material stream 37 comprising extraction medium and water is preferably passed back to the extractive distillation.

If the butadiene is obtained via a side takeoff, the extraction solution thus taken off is transferred to a desorption zone, wherein the butadiene is further desorbed from the extraction solution and backwashed. The desorption zone can be designed, for example, in the form of a scrubbing column which has 2 to 30, preferably 5 to 20, theoretical plates and optionally a backwash zone having, for example, 4 theoretical plates. This backwash zone serves for recovery of the extraction medium present in the gas phase using a liquid hydrocarbon reflux, for which purpose the overhead fraction is condensed in advance. As internals, structured packings, trays or random packings are provided. The distillation is preferably carried out at a sump temperature in the range from 100 to 300° C., in particular in the range from 150 to 200° C. and a top temperature in the range from 0 to 70° C., in particular in the range from 10 to 50° C. The pressure in the distillation column is in this case preferably in the range from 1 to 10 bar. Generally, in the desorption zone a reduced pressure compared with the extraction zone prevails and/or an elevated temperature compared with the extraction zone prevails.

Valuable product stream 38 obtained at the column top generally comprises 90 to 100% by volume of butadiene, 0 to 10% by volume 2-butene and 0 to 10% by volume n-butane and isobutane. For further purification of the butadiene, a further distillation of the prior art can be carried out.

EXAMPLES

Comparative Example

The claimed technical solution was developed via thermodynamic equilibrium step simulations and examined in a pilot plant.

In this pilot plant the salt bath reactor, the organic quench, the compressor unit and also the $C_4$-absorption/desorption were reproduced. The scale of the pilot plant was selected in such a manner that up-scaling to a large-scale plant is possible. For example the internals of the columns were selected and the loops were closed accordingly representatively. The pilot plant was able to produce between 500 and 1500 grams of butadiene per hour.

When the plant is operated with 8% butene at the reactor input and 6% oxygen at the reactor outlet, solids formations occurred in the steam generator M. These were not even able to be prevented by ejecting 10% of the water stream via the purge stream 22 and replacing it with fresh water. The substances present in the circulation water are cracked in the steam generator and are deposited there and in the subsequent lines.

The substances responsible for the deposits were analyzed in the water circuit stream and are given in table 1 below.

TABLE 1

| Name | % by mass |
|---|---|
| Acrolein | 0.060 |
| Methacrolein | 0.115 |
| 3-Hydroxypropanal | 0.185 |
| Furan derivatives | 0.002 |
| Other low-boiling minor components | 0.184 |
| Absorption medium | 0.053 |
| Water | 99.400 |

Example 1a

As shown in FIG. 1, a column L was introduced between the phase separator I and the steam generator M. In this column L, by stripping with nitrogen, the fraction of highly volatile components in the steam condensate was reduced to the level given in table 2. The water thus treated could then be vaporized in the steam generator without a significant amount of solid forming. The composition of the streams is reproduced in the following table 2.

TABLE 2

| Stream: | | 12 | 16 | 17 | 18 | 19 | 20 | 21 |
|---|---|---|---|---|---|---|---|---|
| Temperature | °C. | 54.1 | 32.5 | 52.9 | 35.0 | 60.0 | 148.4 | 30.0 |
| Pressure | bar | 10.0 | 10.0 | 10.0 | 10.0 | 5.5 | 5.5 | 10.3 |
| Mass stream | kg/h | 9.5 | 8.3 | 22.0 | 0.3 | 22.0 | 22.9 | 22.9 |
| BUTANE | % by weight | 3.34 | 0.55 | 1.25 | 0.00 | 1.25 | 0.01 | 0.01 |
| ISOBUTANE | | 0.74 | 0.10 | 0.28 | 0.00 | 0.28 | 0.00 | 0.00 |
| 1-BUTENE | | 0.02 | 0.00 | 0.01 | 0.00 | 0.01 | 0.00 | 0.00 |
| C-2-BUTENE | | 0.58 | 0.01 | 0.25 | 0.00 | 0.25 | 0.00 | 0.00 |
| T-2-BUTENE | | 1.36 | 0.02 | 0.58 | 0.00 | 0.58 | 0.01 | 0.01 |
| 1,3-BUTADIENE | | 9.65 | 0.41 | 4.09 | 0.00 | 4.09 | 0.05 | 0.05 |
| H2O | | 0.87 | 0.30 | 0.36 | 0.00 | 0.38 | 10.57 | 10.57 |
| ACROLEIN | | 0.17 | 0.10 | 0.54 | 0.00 | 0.54 | 0.51 | 0.51 |
| ACETALDEHYDE | | 0.13 | 0.01 | 0.07 | 0.00 | 0.07 | 0.02 | 0.02 |
| MAC | | 0.28 | 0.21 | 0.88 | 0.00 | 0.88 | 0.84 | 0.84 |
| TMB | | 0.54 | 0.21 | 91.29 | 0.00 | 91.29 | 87.86 | 87.86 |
| CO2 | | 0.94 | 1.07 | 0.01 | 0.00 | 0.01 | 0.00 | 0.00 |
| CO | | 0.19 | 0.22 | 0.00 | 0.00 | 0.00 | 0.00 | 0.00 |
| N2 | | 74.78 | 89.59 | 0.15 | 100.00 | 0.15 | 0.00 | 0.00 |
| O2 | | 6.16 | 7.11 | 0.00 | 0.00 | 0.00 | 0.00 | 0.00 |
| Others | | 0.26 | 0.08 | 0.22 | 0.00 | 0.22 | 0.14 | 0.14 |

| Stream: | | 21a | 21b | 21c | 22 | 23 | 24 | 25 |
|---|---|---|---|---|---|---|---|---|
| Temperature | °C. | 30.05 | 30.05 | 26.16 | 30.05 | 156.24 | 35.00 | 30.05 |
| Pressure | bar | 10.20 | 10.10 | 1.00 | 10.20 | 5.62 | 10.20 | 10.10 |
| Mass stream | kg/h | 2.38 | 20.14 | 2.36 | 0.15 | 2.34 | 0.11 | 0.30 |
| BUTANE | % by weight | 0.00 | 0.01 | 0.00 | 0.00 | 0.00 | 0.00 | 0.01 |
| ISOBUTANE | | 0.00 | 0.00 | 0.00 | 0.00 | 0.00 | 0.00 | 0.00 |
| 1-BUTENE | | 0.00 | 0.00 | 0.00 | 0.00 | 0.00 | 0.00 | 0.00 |
| C-2-BUTENE | | 0.00 | 0.01 | 0.00 | 0.00 | 0.00 | 0.00 | 0.01 |
| T-2-BUTENE | | 0.00 | 0.01 | 0.00 | 0.00 | 0.00 | 0.00 | 0.01 |
| 1,3-BUTADIENE | | 0.00 | 0.06 | 0.00 | 0.00 | 0.00 | 0.00 | 0.06 |
| H2O | | 99.58 | 0.04 | 99.85 | 99.58 | 99.85 | 100.00 | 0.04 |
| ACROLEIN | | 0.17 | 0.55 | 0.02 | 0.17 | 0.02 | 0.00 | 0.55 |
| ACETALDEHYDE | | 0.02 | 0.02 | 0.00 | 0.02 | 0.00 | 0.00 | 0.02 |
| MAC | | 0.15 | 0.92 | 0.00 | 0.15 | 0.00 | 0.00 | 0.92 |
| TMB | | 0.01 | 98.25 | 0.00 | 0.01 | 0.00 | 0.00 | 98.25 |
| CO2 | | 0.00 | 0.00 | 0.00 | 0.00 | 0.00 | 0.00 | 0.00 |
| CO | | 0.00 | 0.00 | 0.00 | 0.00 | 0.00 | 0.00 | 0.00 |
| N2 | | 0.00 | 0.00 | 0.08 | 0.00 | 0.08 | 0.00 | 0.00 |
| O2 | | 0.00 | 0.00 | 0.00 | 0.00 | 0.00 | 0.00 | 0.00 |
| Others | | 0.06 | 0.15 | 0.05 | 0.06 | 0.05 | 0.00 | 0.00 |

| Stream: | | 26 | 27 | 28 | 29 | 30 | Off-gas | Nitrogen |
|---|---|---|---|---|---|---|---|---|
| Temperature | °C. | 35.00 | 49.98 | 17.10 | 17.10 | 17.10 | 29.83 | 30.00 |
| Pressure | bar | 10.00 | 5.50 | 5.30 | 5.40 | 5.30 | 1.00 | 1.00 |
| Mass stream | kg/h | 0.24 | 3.39 | 1.41 | 0.08 | 1.90 | 0.52 | 0.50 |

TABLE 2-continued

| | | | | | | | | |
|---|---|---|---|---|---|---|---|---|
| BUTANE | % by weight | 0.00 | 18.63 | 18.83 | 10.44 | 18.83 | 0.00 | 0.00 |
| ISOBUTANE | | 0.00 | 4.19 | 4.21 | 3.48 | 4.21 | 0.00 | 0.00 |
| 1-BUTENE | | 0.00 | 0.12 | 0.12 | 0.07 | 0.12 | 0.00 | 0.00 |
| C-2-BUTENE | | 0.00 | 3.70 | 3.75 | 1.61 | 3.75 | 0.00 | 0.00 |
| T-2-BUTENE | | 0.00 | 8.70 | 8.81 | 4.11 | 8.81 | 0.00 | 0.00 |
| 1,3-BUTADIENE | | 0.00 | 60.37 | 60.96 | 35.86 | 60.96 | 0.00 | 0.00 |
| H2O | | 0.00 | 0.73 | 0.74 | 0.16 | 0.74 | 2.71 | 0.00 |
| ACROLEIN | | 0.00 | 0.15 | 0.15 | 0.01 | 0.15 | 0.72 | 0.00 |
| ACETALDEHYDE | | 0.00 | 0.78 | 0.78 | 0.69 | 0.78 | 0.09 | 0.00 |
| MAC | | 0.00 | 0.18 | 0.18 | 0.01 | 0.18 | 0.70 | 0.00 |
| TMB | | 100.00 | 0.01 | 0.01 | 0.00 | 0.01 | 0.03 | 0.00 |
| CO2 | | 0.00 | 0.06 | 0.04 | 1.00 | 0.04 | 0.00 | 0.00 |
| CO | | 0.00 | 0.00 | 0.00 | 0.00 | 0.00 | 0.00 | 0.00 |
| N2 | | 0.00 | 1.08 | 0.08 | 42.20 | 0.08 | 95.71 | 100.00 |
| O2 | | 0.00 | 0.00 | 0.00 | 0.01 | 0.00 | 0.00 | 0.00 |
| Others | | 0.00 | 0.00 | 0.00 | 0.00 | 0.00 | 0.00 | 0.00 |

Example 1b

As in example 1, nitrogen was introduced into column L 20 as stripping gas. The amount of nitrogen, however, was reduced to 40%. A depletion of the low-boiling minor components was likewise still given thereby. The fraction of minor components separated off, however, decreases here. The composition of the streams is reproduced in the following table 3.

TABLE 3

| Stream: | | 12 | 16 | 17 | 18 | 19 | 20 | 21 |
|---|---|---|---|---|---|---|---|---|
| Temperature | ° C. | 54.1 | 32.4 | 52.9 | 35.0 | 60.0 | 148.3 | 30.0 |
| Pressure | bar | 10.0 | 10.0 | 10.0 | 10.0 | 5.5 | 5.5 | 10.3 |
| Mass stream | kg/h | 9.5 | 8.3 | 22.0 | 0.3 | 22.0 | 22.9 | 22.9 |
| BUTANE | % by weight | 3.34 | 0.54 | 1.25 | 0.00 | 1.25 | 0.01 | 0.01 |
| ISOBUTANE | | 0.74 | 0.10 | 0.28 | 0.00 | 0.28 | 0.00 | 0.00 |
| 1-BUTENE | | 0.02 | 0.00 | 0.01 | 0.00 | 0.01 | 0.00 | 0.00 |
| C-2-BUTENE | | 0.58 | 0.01 | 0.25 | 0.00 | 0.25 | 0.00 | 0.00 |
| T-2-BUTENE | | 1.36 | 0.02 | 0.59 | 0.00 | 0.59 | 0.01 | 0.01 |
| 1,3-BUTADIENE | | 9.65 | 0.40 | 4.09 | 0.00 | 4.09 | 0.05 | 0.05 |
| H2O | | 0.87 | 0.30 | 0.38 | 0.00 | 0.38 | 10.56 | 10.56 |
| ACROLEIN | | 0.17 | 0.12 | 0.59 | 0.00 | 0.59 | 0.57 | 0.57 |
| ACETALDEHYDE | | 0.13 | 0.01 | 0.07 | 0.00 | 0.07 | 0.02 | 0.02 |
| MAC | | 0.28 | 0.22 | 0.90 | 0.00 | 0.90 | 0.85 | 0.85 |
| TMB | | 0.54 | 0.21 | 91.20 | 0.00 | 91.20 | 87.78 | 87.78 |
| CO2 | | 0.94 | 1.07 | 0.01 | 0.00 | 0.01 | 0.00 | 0.00 |
| CO | | 0.19 | 0.22 | 0.00 | 0.00 | 0.00 | 0.00 | 0.00 |
| N2 | | 74.78 | 89.58 | 0.15 | 100.00 | 0.15 | 0.00 | 0.00 |
| O2 | | 6.16 | 7.11 | 0.00 | 0.00 | 0.00 | 0.00 | 0.00 |
| Others | | 0.26 | 0.08 | 0.23 | 0.00 | 0.23 | 0.15 | 0.15 |

| Stream: | | 21a | 21b | 21c | 22 | 23 | 24 | 25 |
|---|---|---|---|---|---|---|---|---|
| Temperature | ° C. | 30.05 | 30.05 | 28.34 | 30.05 | 156.22 | 35.00 | 30.05 |
| Pressure | bar | 10.20 | 10.10 | 1.00 | 10.20 | 5.62 | 10.20 | 10.10 |
| Mass stream | kg/h | 2.37 | 20.14 | 2.36 | 0.15 | 2.34 | 0.10 | 0.30 |
| BUTANE | % by weight | 0.00 | 0.01 | 0.00 | 0.00 | 0.00 | 0.00 | 0.01 |
| ISOBUTANE | | 0.00 | 0.00 | 0.00 | 0.00 | 0.00 | 0.00 | 0.00 |
| 1-BUTENE | | 0.00 | 0.00 | 0.00 | 0.00 | 0.00 | 0.00 | 0.00 |
| C-2-BUTENE | | 0.00 | 0.01 | 0.00 | 0.00 | 0.00 | 0.00 | 0.01 |
| T-2-BUTENE | | 0.00 | 0.01 | 0.00 | 0.00 | 0.00 | 0.00 | 0.01 |
| 1,3-BUTADIENE | | 0.00 | 0.06 | 0.00 | 0.00 | 0.00 | 0.00 | 0.06 |
| H2O | | 99.55 | 0.04 | 99.73 | 99.55 | 99.72 | 100.00 | 0.04 |
| ACROLEIN | | 0.20 | 0.61 | 0.10 | 0.20 | 0.10 | 0.00 | 0.61 |
| ACETALDEHYDE | | 0.03 | 0.02 | 0.02 | 0.03 | 0.02 | 0.00 | 0.02 |
| MAC | | 0.16 | 0.93 | 0.02 | 0.16 | 0.02 | 0.00 | 0.93 |
| TMB | | 0.01 | 98.16 | 0.00 | 0.01 | 0.00 | 0.00 | 98.16 |
| CO2 | | 0.00 | 0.00 | 0.00 | 0.00 | 0.00 | 0.00 | 0.00 |
| CO | | 0.00 | 0.00 | 0.00 | 0.00 | 0.00 | 0.00 | 0.00 |
| N2 | | 0.00 | 0.00 | 0.08 | 0.00 | 0.08 | 0.00 | 0.00 |
| O2 | | 0.00 | 0.00 | 0.00 | 0.00 | 0.00 | 0.00 | 0.00 |
| Others | | 0.07 | 0.15 | 0.06 | 0.07 | 0.06 | 0.00 | 0.00 |

| Stream: | | 26 | 27 | 28 | 29 | 30 | Off-gas | Nitrogen |
|---|---|---|---|---|---|---|---|---|
| Temperature | ° C. | 35.00 | 50.02 | 17.10 | 17.10 | 17.10 | 30.00 | 30.00 |
| Pressure | bar | 10.00 | 5.50 | 5.30 | 5.40 | 5.30 | 1.00 | 1.00 |
| Mass stream | kg/h | 0.24 | 3.39 | 1.41 | 0.08 | 1.90 | 0.21 | 0.20 |
| BUTANE | % by weight | 0.00 | 18.64 | 18.84 | 10.44 | 18.84 | 0.00 | 0.00 |
| ISOBUTANE | | 0.00 | 4.19 | 4.21 | 3.48 | 4.21 | 0.00 | 0.00 |
| 1-BUTENE | | 0.00 | 0.12 | 0.12 | 0.07 | 0.12 | 0.00 | 0.00 |

TABLE 3-continued

| | | | | | | | |
|---|---|---|---|---|---|---|---|
| C-2-BUTENE | 0.00 | 3.69 | 3.74 | 1.61 | 3.74 | 0.00 | 0.00 |
| T-2-BUTENE | 0.00 | 8.70 | 8.81 | 4.11 | 8.81 | 0.00 | 0.00 |
| 1,3-BUTADIENE | 0.00 | 60.33 | 60.93 | 35.84 | 60.93 | 0.00 | 0.00 |
| H2O | 0.00 | 0.73 | 0.75 | 0.16 | 0.75 | 2.72 | 0.00 |
| ACROLEIN | 0.00 | 0.17 | 0.17 | 0.01 | 0.17 | 1.07 | 0.00 |
| ACETALDEHYDE | 0.00 | 0.79 | 0.79 | 0.70 | 0.79 | 0.11 | 0.00 |
| MAC | 0.00 | 0.18 | 0.18 | 0.01 | 0.18 | 1.57 | 0.00 |
| TMB | 100.00 | 0.01 | 0.01 | 0.00 | 0.01 | 0.07 | 0.00 |
| CO2 | 0.00 | 0.06 | 0.04 | 1.00 | 0.04 | 0.00 | 0.00 |
| CO | 0.00 | 0.00 | 0.00 | 0.00 | 0.00 | 0.00 | 0.00 |
| N2 | 0.00 | 1.08 | 0.08 | 42.20 | 0.08 | 94.40 | 100.00 |
| O2 | 0.00 | 0.00 | 0.00 | 0.01 | 0.00 | 0.00 | 0.00 |
| Others | 0.00 | 0.00 | 0.00 | 0.00 | 0.00 | 0.00 | 0.00 |

Example 2

As shown in FIG. 1, a column L was introduced between the phase separator I and the steam generator M. In this column L, by stripping with nitrogen and heating to approximately 50° C. at 1 bar, the fraction of highly volatile components in the water was reduced to the level given in table 4. The water thus treated could then be vaporized in the steam generator without significant amounts of solids forming. The composition of the streams is reproduced in the following table 4.

TABLE 4

| Stream: | | 12 | 16 | 17 | 18 | 19 | 20 | 21 |
|---|---|---|---|---|---|---|---|---|
| Temperature | ° C. | 54.1 | 32.5 | 52.9 | 35.0 | 60.0 | 148.4 | 30.0 |
| Pressure | bar | 10.0 | 10.0 | 10.0 | 10.0 | 5.5 | 5.5 | 10.3 |
| Mass stream | kg/h | 9.5 | 8.3 | 22.0 | 0.3 | 22.0 | 22.9 | 22.9 |
| BUTANE | % by weight | 3.34 | 0.55 | 1.25 | 0.00 | 1.25 | 0.01 | 0.01 |
| ISOBUTANE | | 0.74 | 0.10 | 0.28 | 0.00 | 0.28 | 0.00 | 0.00 |
| 1-BUTENE | | 0.02 | 0.00 | 0.01 | 0.00 | 0.01 | 0.00 | 0.00 |
| C-2-BUTENE | | 0.58 | 0.01 | 0.25 | 0.00 | 0.25 | 0.00 | 0.00 |
| T-2-BUTENE | | 1.36 | 0.02 | 0.58 | 0.00 | 0.58 | 0.01 | 0.01 |
| 1,3-BUTADIENE | | 9.65 | 0.41 | 4.09 | 0.00 | 4.09 | 0.05 | 0.05 |
| H2O | | 0.87 | 0.30 | 0.38 | 0.00 | 0.38 | 10.57 | 10.57 |
| ACROLEIN | | 0.17 | 0.10 | 0.53 | 0.00 | 0.53 | 0.50 | 0.50 |
| ACETALDEHYDE | | 0.13 | 0.01 | 0.07 | 0.00 | 0.07 | 0.02 | 0.02 |
| MAC | | 0.28 | 0.21 | 0.88 | 0.00 | 0.88 | 0.84 | 0.84 |
| TMB | | 0.54 | 0.21 | 91.29 | 0.00 | 91.29 | 87.86 | 87.86 |
| CO2 | | 0.94 | 1.07 | 0.01 | 0.00 | 0.01 | 0.00 | 0.00 |
| CO | | 0.19 | 0.22 | 0.00 | 0.00 | 0.00 | 0.00 | 0.00 |
| N2 | | 74.78 | 89.59 | 0.15 | 100.00 | 0.15 | 0.00 | 0.00 |
| O2 | | 6.16 | 7.11 | 0.00 | 0.00 | 0.00 | 0.00 | 0.00 |
| Others | | 0.26 | 0.08 | 0.22 | 0.0 | 0.22 | 0.14 | 0.14 |

| Stream: | | 21a | 21b | 21c | 22 | 23 | 24 | 25 |
|---|---|---|---|---|---|---|---|---|
| Temperature | ° C. | 30.05 | 30.05 | 49.73 | 30.05 | 156.24 | 35.00 | 30.05 |
| Pressure | bar | 10.20 | 10.10 | 1.00 | 10.20 | 5.62 | 10.20 | 10.10 |
| Mass stream | kg/h | 2.38 | 20.14 | 2.36 | 0.15 | 2.34 | 0.11 | 0.30 |
| BUTANE | % by weight | 0.00 | 0.01 | 0.00 | 0.00 | 0.00 | 0.00 | 0.01 |
| ISOBUTANE | | 0.00 | 0.00 | 0.00 | 0.00 | 0.00 | 0.00 | 0.00 |
| 1-BUTENE | | 0.00 | 0.00 | 0.00 | 0.00 | 0.00 | 0.00 | 0.00 |
| C-2-BUTENE | | 0.00 | 0.01 | 0.00 | 0.00 | 0.00 | 0.00 | 0.01 |
| T-2-BUTENE | | 0.00 | 0.01 | 0.00 | 0.00 | 0.00 | 0.00 | 0.01 |
| 1,3-BUTADIENE | | 0.00 | 0.06 | 0.00 | 0.00 | 0.00 | 0.00 | 0.06 |
| H2O | | 99.58 | 0.03 | 99.86 | 99.58 | 99.86 | 100.00 | 0.03 |
| ACROLEIN | | 0.17 | 0.54 | 0.01 | 0.17 | 0.01 | 0.00 | 0.54 |
| ACETALDEHYDE | | 0.02 | 0.02 | 0.00 | 0.02 | 0.00 | 0.00 | 0.02 |
| MAC | | 0.15 | 0.92 | 0.00 | 0.15 | 0.00 | 0.00 | 0.92 |
| TMB | | 0.01 | 98.26 | 0.00 | 0.01 | 0.00 | 0.00 | 98.26 |
| CO2 | | 0.00 | 0.00 | 0.00 | 0.00 | 0.00 | 0.00 | 0.00 |
| CO | | 0.00 | 0.00 | 0.00 | 0.00 | 0.00 | 0.00 | 0.00 |
| N2 | | 0.00 | 0.00 | 0.08 | 0.00 | 0.08 | 0.00 | 0.00 |
| O2 | | 0.00 | 0.00 | 0.00 | 0.00 | 0.00 | 0.00 | 0.00 |
| Others | | 0.06 | 0.15 | 0.05 | 0.06 | 0.05 | 0.00 | 0.15 |

| Stream: | | 26 | 27 | 28 | 29 | 30 | Off-gas | Nitrogen |
|---|---|---|---|---|---|---|---|---|
| Temperature | ° C. | 35.00 | 49.98 | 17.10 | 17.10 | 17.10 | 30.00 | 30.00 |
| Pressure | bar | 10.00 | 5.50 | 5.30 | 5.40 | 5.30 | 1.00 | 1.00 |
| Mass stream | kg/h | 0.24 | 3.39 | 1.41 | 0.08 | 1.90 | 0.52 | 0.50 |
| BUTANE | % by weight | 0.00 | 18.63 | 18.83 | 10.44 | 18.83 | 0.00 | 0.00 |
| ISOBUTANE | | 0.00 | 4.19 | 4.21 | 3.48 | 4.21 | 0.00 | 0.00 |
| 1-BUTENE | | 0.00 | 0.12 | 0.12 | 0.07 | 0.12 | 0.00 | 0.00 |
| C-2-BUTENE | | 0.00 | 3.70 | 3.75 | 1.61 | 3.75 | 0.00 | 0.00 |

TABLE 4-continued

| | | | | | | | |
|---|---|---|---|---|---|---|---|
| T-2-BUTENE | 0.00 | 8.70 | 8.82 | 4.11 | 8.82 | 0.00 | 0.00 |
| 1,3-BUTADIENE | 0.00 | 60.37 | 60.96 | 35.86 | 60.96 | 0.00 | 0.00 |
| H2O | 0.00 | 0.73 | 0.74 | 0.16 | 0.74 | 2.74 | 0.00 |
| ACROLEIN | 0.00 | 0.15 | 0.15 | 0.01 | 0.15 | 0.74 | 0.00 |
| ACETALDEHYDE | 0.00 | 0.77 | 0.78 | 0.69 | 0.78 | 0.10 | 0.00 |
| MAC | 0.00 | 0.18 | 0.18 | 0.01 | 0.18 | 0.71 | 0.00 |
| TMB | 100.00 | 0.01 | 0.01 | 0.00 | 0.01 | 0.03 | 0.00 |
| CO2 | 0.00 | 0.06 | 0.04 | 1.00 | 0.04 | 0.00 | 0.00 |
| CO | 0.00 | 0.00 | 0.00 | 0.00 | 0.00 | 0.00 | 0.00 |
| N2 | 0.00 | 1.08 | 0.08 | 42.20 | 0.08 | 95.65 | 100.00 |
| O2 | 0.00 | 0.00 | 0.00 | 0.01 | 0.00 | 0.00 | 0.00 |
| Others | 0.00 | 1.30 | 1.32 | 0.34 | 1.32 | 0.03 | 0.00 |

The invention claimed is:

1. A method for producing butadiene from n-butenes having the steps:
A) providing a feed gas stream a comprising the n-butenes;
B) feeding the feed gas stream a and an oxygen-comprising gas into an oxidative dehydrogenation zone to oxidatively dehydrogenating n-butenes to butadiene and obtaining a product gas stream b comprising butadiene, unreacted n-butenes, steam, oxygen, low-boiling hydrocarbons, high-boiling minor components, optionally carbon oxides and optionally inert gases;
Ca) cooling the product gas stream b by contacting it with a refrigerant and condensing at least a part of the high-boiling minor components;
Cb) compressing the cooled product gas stream b in at least one compression step and obtaining at least one aqueous condensate stream c1 and a gas stream c2 comprising butadiene, n-butenes, steam, oxygen, low-boiling hydrocarbons, optionally carbon oxides and optionally inert gases;
Da) absorbing the $C_4$ hydrocarbons butadiene and n-butenes in an absorption medium to produce an absorption medium stream loaded with $C_4$ hydrocarbons and a gas stream d2 comprising oxygen, low-boiling hydrocarbons, optionally carbon oxides and optionally inert gases;
Db) desorbing the $C_4$ hydrocarbons from the loaded absorption medium stream in a desorption column by stripping with stream and obtaining a $C_4$ product gas stream d1 and a liquid mixture comprising absorption medium and steam condensate;
Dc1) separating off the steam condensate from the absorption medium in a phase separator;
Dc2) pretreating the steam condensate by stripping with a stripping gas, by heating, or by stripping and heating to remove low-boiling minor components from the steam condensate; and
Dc3) vaporizing the pretreated steam condensate in a steam generator, and providing the steam as stripping gas in the desorption column.

2. The method according to claim 1 having the additional steps:
E) separating the $C_4$ product stream d1 by extractive distillation using a solvent selective for butadiene into a material stream e1 comprising butadiene and the selective solvent and a material stream e2 comprising n-butenes;
F) distilling the butadiene and the material stream f2 comprising the selective solvent into a material stream g1 substantially comprising the selective solvent and a material stream g2 comprising butadiene.

3. The method according to claim 1, wherein the low-boiling minor components are separated off from the steam condensate by stripping with nitrogen.

4. The method according to claim 3, wherein the stripping with nitrogen is performed at a temperature from 0 to 150° C. and a pressure from 1 to 10 000 mbar.

5. The method according to claim 1, wherein the low-boiling minor components are selected from the group consisting of acrolein, methacrolein and 3-hydroxypropanal.

6. The method according to claim 1, wherein the oxygen-comprising gas fed in step B) comprises at least 90% by volume of oxygen.

7. The method according to claim 1, wherein the gas stream d2 that is separated off in step Da) is recycled at least in part in step B).

8. The method according to claim 1, wherein:
the absorption medium stream loaded with $C_4$ hydrocarbons from step Da) is stripped with a non-condensable gas to remove oxygen from the absorption medium stream loaded with $C_4$ hydrocarbons, and the $C_4$ product gas stream d1 obtained from step Db) comprises less than 100 ppm of oxygen.

9. The method according to claim 1, wherein the absorption medium used in step Da) is an aromatic hydrocarbon solvent.

* * * * *